US010676461B2

(12) United States Patent
Nagai et al.

(10) Patent No.: US 10,676,461 B2
(45) Date of Patent: Jun. 9, 2020

(54) HETEROCYCLIC COMPOUND

(71) Applicant: TAKEDA PHARMACEUTICAL COMPANY LIMITED, Osaka-shi, Osaka (JP)

(72) Inventors: Katsunori Nagai, Fujisawa (JP); Takuto Kojima, Fujisawa (JP); Shinichi Imamura, Fujisawa (JP); Masao Hirakata, Fujisawa (JP)

(73) Assignee: TAKEDA PHARMACEUTICAL COMPANY LIMITED, Osaka-shi, Osaka (JP)

( * ) Notice: Subject to any disclaimer, the term of this patent is extended or adjusted under 35 U.S.C. 154(b) by 0 days.

(21) Appl. No.: 16/342,892

(22) PCT Filed: Oct. 17, 2017

(86) PCT No.: PCT/JP2017/037503
§ 371 (c)(1),
(2) Date: Apr. 17, 2019

(87) PCT Pub. No.: WO2018/074461
PCT Pub. Date: Apr. 26, 2018

(65) Prior Publication Data
US 2019/0263784 A1    Aug. 29, 2019

(30) Foreign Application Priority Data

Oct. 18, 2016   (JP) ................. 2016-204371

(51) Int. Cl.
| | | |
|---|---|---|
| *C07D 401/14* | (2006.01) | |
| *A61P 3/00* | (2006.01) | |
| *A61P 35/00* | (2006.01) | |
| *A61K 9/00* | (2006.01) | |
| *A61K 31/05* | (2006.01) | |
| *A61K 31/09* | (2006.01) | |
| *A61K 31/57* | (2006.01) | |
| *A61K 31/58* | (2006.01) | |
| *A61K 31/6615* | (2006.01) | |
| *A61P 43/00* | (2006.01) | |
| *A61K 31/498* | (2006.01) | |
| *A61K 45/06* | (2006.01) | |

(52) U.S. Cl.
CPC .......... *C07D 401/14* (2013.01); *A61K 9/0019* (2013.01); *A61K 9/0053* (2013.01); *A61K 31/05* (2013.01); *A61K 31/09* (2013.01); *A61K 31/498* (2013.01); *A61K 31/57* (2013.01); *A61K 31/58* (2013.01); *A61K 31/6615* (2013.01); *A61P 3/00* (2018.01); *A61P 35/00* (2018.01); *A61P 43/00* (2018.01); *A61K 45/06* (2013.01)

(58) Field of Classification Search
CPC .................................................. C07D 401/14
See application file for complete search history.

(56) References Cited

U.S. PATENT DOCUMENTS

| | | |
|---|---|---|
| 6,492,393 B1 | 12/2002 | Breitfelder et al. |
| 7,241,758 B2 | 7/2007 | Hao et al. |
| 8,470,816 B2 | 6/2013 | Ikeura et al. |
| 8,592,454 B2 | 11/2013 | Shirai et al. |
| 8,697,739 B2 | 4/2014 | Barnes et al. |
| 2006/0079542 A1 | 4/2006 | Nestor |
| 2007/0135450 A1 | 6/2007 | Nestor |
| 2008/0287479 A1 | 11/2008 | Hutchings et al. |
| 2009/0042772 A1 | 2/2009 | Nestor |
| 2009/0156572 A1 | 6/2009 | Ikeura et al. |
| 2014/0171363 A1 | 6/2014 | Barnes et al. |
| 2014/0243286 A1 | 8/2014 | Arnold et al. |
| 2018/0170874 A1 | 6/2018 | Asano et al. |

FOREIGN PATENT DOCUMENTS

| | | |
|---|---|---|
| WO | WO 97/45119 A1 | 5/1997 |
| WO | WO 2008/038841 A1 | 4/2008 |
| WO | WO 2009/072643 A1 | 6/2009 |

OTHER PUBLICATIONS

McMahon et al. (2000).*
Pinedo et al. (2000).*
Barelier et al., "Fragment-based deconstruction of Bcl-xL inhibitors." J Med Chem. Mar. 25, 2010;53(6):2577-88.
Database Caplus [Online], Chemical Abstracts Service, Columbus, Ohio, US; Apr. 3, 2008, Japan Tobacco Inc., Japan: "Preparation of thiadiazolone derivatives as TNF-.alpha. converting enzyme (TACE) inhibitors." Database accession No. 2008: 410465, 13 pages.
Extended European Search Report in EP Application No. 16783163. 5, dated Sep. 11, 2018, 7 pages.
International Search Report mailed in International Patent Application No. PCT/JP2016/062418, dated Jul. 19, 2016.
International Search Report mailed in International Patent Application No. PCT/JP2017/037503, dated Dec. 26, 2017.
Lee et al., "Myriocin, a serine palmitoyltransferase inhibitor, suppresses tumor growth in a murine melanoma model by inhibiting de novo sphingolipid synthesis," Cancer Biol. Ther., 13(2): 92-100 (2012).
Notice of Allowance in U.S. Appl. No. 15/565,891, dated Aug. 3, 2018.
Restriction/Election Requirement in U.S. Appl. No. 15/565,891, dated May 10, 2018.

(Continued)

*Primary Examiner* — Paul V Ward
(74) *Attorney, Agent, or Firm* — Casimir Jones, S.C.; Anne M. Reynolds

(57) ABSTRACT

The present invention relates to N-((3S,4R)-1-((8-chloroquinoxalin-6-yl)carbonyl)-3-(4-fluorophenyl)piperidin-4-yl)-1-methyl-5-(trifluoromethyl)-1H-pyrazole-3-carboxamide, which is a compound that can be useful for the treatment or prevention of SPT-related diseases including congenital diseases associated with the storage of sphingolipids, such as cancer and Niemann-Pick disease, or a salt thereof.

5 Claims, 1 Drawing Sheet

(56) References Cited

OTHER PUBLICATIONS

Yaguchi, et al. "Antitumor activity of a novel and orally available inhibitor of serine palmitoyltransferase." Biochemical and Biophysical Research Communications, 2017, 484(3):493-500.
International Preliminary Report on Patentability, English Translation, PCT/JP2017/037503, dated May 2, 2019, 7 pages.
Israeli Office Action dated Jan. 23, 2020, Israel Patent Application No. 254890, 3 pages.

* cited by examiner

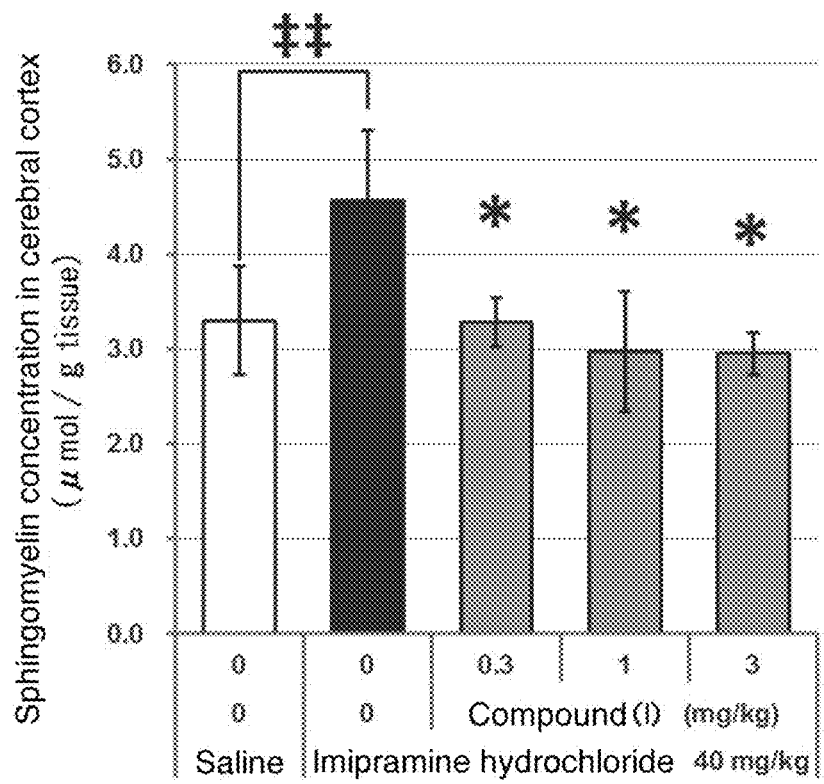
‡‡ p ≤ 0.01 vs. control (saline, intraperitoneal administration) in Student's t-test
* p ≤ 0.025 vs. vehicle (0.5% MC, oral administration) in one-tailed Williams' test
Mean ± S.D., N=7-8.

HETEROCYCLIC COMPOUND

TECHNICAL FIELD

The present invention relates to a novel compound or a salt thereof which can have an inhibitory effect on serine palmitoyltransferase (hereinafter, also referred to as "SPT"). The present invention further relates to a medicament which can be useful for the prevention or treatment of SPT-related diseases including cancer and congenital diseases associated with sphingolipid accumulation including Niemann-Pick disease, etc., comprising the compound or a salt thereof.

BACKGROUND OF THE INVENTION

SPT is an enzyme that catalyzes the reaction through which L-serine and palmitoyl coenzyme A are condensed to synthesize 3-ketodihydrosphingosine, and is involved in the biosynthesis of sphingolipids. SPT is constituted by a plurality of subunits. 3 types of SPT subunits are known: SPT1 (also called SPTLC1), SPT2 (also called SPTLC2) and SPT3 (also called SPTLC3). From the perspective of a complex of subunits, a complex consisting of subunits SPT1 and SPT2 and a complex consisting of subunits SPT1 and SPT3 are known as SPT.

The sphingolipids include ceramide, sphingomyelin, ganglioside and the like. The sphingolipids are constituents of cell membranes and are known to play an important role in maintenance of homeostasis of the membranes and signal transduction while having various physiological activities. Myriocin, which has an inhibitory effect on SPT, is known to inhibit the growth of activated lymphocytes, to inhibit the growth of mouse melanoma cell lines, and to exhibit an antitumor effect on mouse melanoma tumor models (Non Patent Literature 1).

Compounds described in Patent Literatures 1 to 6, etc., have been known so far as compounds having an antitumor effect.

PRIOR ART DOCUMENTS

Patent Literature

Patent Document 1: International Publication No. WO2010/032856 pamphlet
Patent Document 2: International Publication No. WO2009/072643 pamphlet
Patent Document 3: International Publication No. WO2008/038841 pamphlet
Patent Document 4: International Publication No. WO2013/033270 pamphlet
Patent Document 5: International Publication No. WO2012/013716 pamphlet
Patent Document 6: International Publication No. WO2001/036403 pamphlet

Non Patent Document

Non Patent Document 1: Cancer Biology & Therapy 2012, 13: 92-100

SUMMARY OF INVENTION

Technical Problem

An object of the present invention is to provide a compound that has an excellent SPT inhibitory effect and can be useful in the prevention or treatment of SPT-related diseases including cancer and congenital diseases associated with sphingolipid accumulation including Niemann-Pick disease, etc.

Solution to Problem

The present inventors have conducted diligent studies in light of the object described above and consequently completed the present invention by finding that a compound represented by the formula (I) given below can have the activity of inhibiting SPT.

[Formula 1]

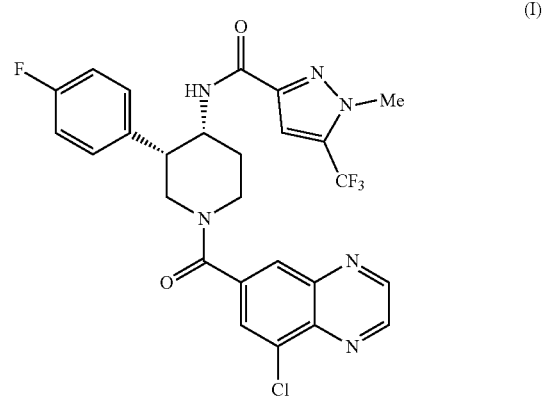

(I)

Specifically, the present invention relates to at least the following aspects:

[1] N-((3S,4R)-1-((8-Chloroquinoxalin-6-yl)carbonyl)-3-(4-fluorophenyl)piperidin-4-yl)-1-methyl-5-(trifluoromethyl)-1H-pyrazole-3-carboxamide or a salt thereof, which may be abbreviated as "compound (I)" hereinafter.

[2] A medicament comprising a compound or a salt thereof according to [1].

[3] The medicament according to [2], wherein the medicament is a SPT inhibitor.

[4] The medicament according to [2], wherein the medicament is a prophylactic or therapeutic agent for cancer.

[5] The medicament according to [2], wherein the medicament is a prophylactic or therapeutic agent for Niemann-Pick disease.

[6] The medicament according to [2], wherein the medicament is a prophylactic or therapeutic agent for Niemann-Pick disease type A or Niemann-Pick disease type B.

[7] The compound or a salt thereof according to [1] for use in the prevention or treatment of cancer.

[8] The compound or a salt thereof according to [1] for use in the prevention or treatment of Niemann-Pick disease.

[9] The compound or a salt thereof according to [1] for use in the prevention or treatment of Niemann-Pick disease type A or Niemann-Pick disease type B.

[10] A method for inhibiting SPT in a mammal, comprising administering an effective amount of a compound or a salt thereof according to [1] to the mammal.

[11] A method for preventing or treating cancer in a mammal, comprising administering an effective amount of a compound or a salt thereof according to [1] to the mammal.

[12] A method for preventing or treating Niemann-Pick disease in a mammal, comprising administering an effective amount of a compound or a salt thereof according to [1] to the mammal.

[13] A method for preventing or treating Niemann-Pick disease type A or Niemann-Pick disease type B in a mammal, comprising administering an effective amount of a compound or a salt thereof according to [1] to the mammal.

[14] Use of a compound or a salt thereof according to [1] for the production of a prophylactic or therapeutic agent for cancer.

[15] Use of a compound or a salt thereof according to [1] for the production of a prophylactic or therapeutic agent for Niemann-Pick disease.

[16] Use of a compound or a salt thereof according to [1] for the production of a prophylactic or therapeutic agent for Niemann-Pick disease type A or Niemann-Pick disease type B.

Advantageous Effects of Invention

The compound or the medicament of the present invention can have an excellent inhibitory effect on SPT. Thus, the compound or the medicament of the present invention can be used as a SPT inhibitor and can be useful as a prophylactic or therapeutic agent for diseases that are probably influenced by SPT, for example, cancer and Niemann-Pick disease.

BRIEF DESCRIPTION OF DRAWINGS

FIG. 1 is a graph showing the test results in Test Example 4 by which the sphingomyelin-lowering effect of the compound of the present invention was confirmed.

DETAILED DESCRIPTION OF THE INVENTION

Hereinafter, the compound of the present invention, a method for producing the same and use of the same will be described in detail.

The salt of the compound (I) is preferably a pharmacologically acceptable salt. Examples thereof include an inorganic acid salt, an organic acid salt and an acidic amino acid salt.

Preferable examples of the inorganic acid salt include a hydrochloride, a hydrobromate, a nitrate, a sulfate and a phosphate.

Preferable examples of the organic acid salt include a formate, an acetate, a trifluoroacetate, a phthalate, a fumarate, an oxalate, a tartarate, a malate, a citrate, a succinate, a malate, a methanesulfonate, a benzenesulfonate and a p-toluenesulfonate.

Preferable examples of the acidic amino acid salt include an aspartate or glutamate.

The compound of the present invention can be produced by, for example, a method described in Example 1.

The compound (I) can be converted to a free form or a different salt of interest by a method known per se in the art or a method equivalent thereto The compound (I) may be crystalline. A single crystal form and a mixture of crystal forms are both included in the compound (I). The crystals can be produced through crystallization by the application of a crystallization method known per se in the art.

Also, the compound (I) may be a pharmaceutically acceptable cocrystal or cocrystal salt. In this context, the cocrystal or the cocrystal salt means a crystalline substance constituted by two or more unique solids at room temperature, each having distinctive physical properties (e.g., structure, melting point, heat of melting, hygroscopicity, stability). The cocrystal and the cocrystal salt can be produced according to a cocrystallization method known per se in the art.

The compound (I) may be a hydrate, a non-hydrate, a solvate or a non-solvate. All of them are included in the compound (I).

A compound labeled or substituted with an isotope (e.g., $^2H$, $^3H$, $^{11}C$, $^{14}C$, $^{18}F$, $^{35}S$, $^{125}I$) or the like is also included in the compound (I). The compound (I) labeled or substituted with an isotope can be used as, for example, a tracer (PET tracer), in positron emission tomography (PET) and can be useful in fields of medical diagnosis and the like.

The compound (I) can have SPT inhibitory activity and can be useful as a prophylactic or therapeutic agent for cancer, a cancer growth inhibitor, a cancer metastasis inhibitor, a prophylactic or therapeutic agent for Niemann-Pick disease, an anti-inflammatory agent, an immunomodulatory agent, an antianxiety agent and an anticonvulsant agent.

The compound (I) can have selective inhibitory activity against SPT. In addition, the compound (I) can be expected to be also excellent in efficacy, pharmacokinetics (e.g., absorbability, distribution, metabolism, excretion), solubility (e.g., water solubility), interaction with other medicaments (e.g., drug-metabolizing enzyme inhibitory effect), safety (e.g., acute toxicity, chronic toxicity, genotoxicity, reproductive toxicity, cardiotoxicity, carcinogenicity, central toxicity) and stability (e.g., chemical stability, stability against enzymes) and can be therefore useful as a medicament.

The compound (I) can have selective inhibitory activity against SPT and be therefore useful as a prophylactic or therapeutic agent for cancer with reduced toxicity to normal cells.

Thus, the compound (I) is capable of inhibiting excessive (abnormal) SPT effects in a mammal (e.g., a mouse, a rat, a hamster, a rabbit, a cat, a dog, cattle, sheep, a monkey, a human).

The compound (I) can be used as a medicament such as a prophylactic or therapeutic agent for diseases that are probably influenced by SPT, which may be herein referred to as "SPT-related diseases", for example, cancer [e.g., large intestine cancer (e.g., colon cancer, rectal cancer, anus cancer, familial colorectal cancer, hereditary non-polyposis colorectal cancer, gastrointestinal stromal tumor), lung cancer (e.g., non-small cell lung cancer (lung adenocarcinoma, etc.), small-cell lung cancer, malignant mesothelioma), mesothelioma, pancreatic cancer (e.g., ductal pancreatic cancer, pancreatic endocrine tumor), throat cancer, voice box cancer, head and neck cancer, esophageal cancer, stomach cancer (e.g., papillary adenocarcinoma, mucous adenocarcinoma, adenosquamous carcinoma), duodenal cancer, small intestine cancer, breast cancer (e.g., invasive ductal breast cancer, noninvasive ductal breast cancer, inflammatory breast cancer), ovarian cancer (e.g., epithelial ovarian cancer, extragonadal germ cell tumor, ovarian germ cell tumor, ovarian tumor of low malignant potential), testicular tumor, prostate cancer (e.g., hormone-dependent prostate cancer, hormone-independent prostate cancer, castration-resistant prostate cancer), liver cancer (e.g., hepatocellular cancer, primary liver cancer, extrahepatic bile duct cancer), thyroid cancer (e.g., medullary thyroid cancer), kidney cancer (e.g., renal cell cancer (e.g., clear cell renal cell carcinoma), transitional cell cancer of the renal pelvis and ureter), uterine cancer (e.g., uterine cervical cancer, uterine body cancer, uterine sarcoma), gestational choriocarcinoma, brain tumor (e.g., medulloblastoma, glioma, pineal astrocytoma, pilocytic astrocytoma, diffuse astrocytoma, anaplastic astrocytoma, pituitary adenoma), retinoblastoma, skin cancer (e.g., basalioma, malignant melanoma), sarcoma (e.g., rhabdomyosarcoma, leiomyosarcoma, soft tissue sarcoma, spindle cell sarcoma), malignant bone tumor, bladder cancer, blood cancer (e.g., multiple myeloma, leukemia, malignant lymphoma, Hodgkin disease, chronic myeloproliferative disease), primary unknown cancer], a cancer growth inhibitor, a cancer metastasis inhibitor, an apoptosis promoter, a therapeutic agent for premalignant lesions (e.g., myelodysplastic syndrome) or the like.

The compound of the present invention can also be useful as a prophylactic agent or a therapeutic agent for other SPT-related diseases (e.g., heart diseases (cardiomegaly, acute heart failure and chronic heart failure including congestive heart failure, cardiomyopathy, angina pectoris, myocarditis, arrhythmia, tachycardia, myocardial infarction, etc.), myocardial ischemia, venous insufficiency, post-myocardial infarction heart failure, hypertension, cor pulmonale, arteriosclerosis including atherosclerosis (aneurysm, coronary arteriosclerosis, cerebral arteriosclerosis, peripheral arteriosclerosis, etc.), vascular hypertrophy, vascular hypertrophy or occlusion and organ disorder after intervention (percutaneous transluminal coronary angioplasty, stent placement, coronary angioscopy, intravascular ultrasonography, intracoronary thrombolytic therapy, etc.), vascular reocclusion or restenosis after bypass surgery, respiratory diseases (acute pulmonary disorder), bone diseases (nonmetabolic bone diseases such as fracture, refracture, bone deformity or osteoarthritis, osteosarcoma, myeloma, dysostosis, scoliosis and the like; bone defect, osteoporosis, osteomalacia, rachitis, osteitis fibrosa, renal osteodystrophy, Behcet's disease in bone, ankylosing spondylitis, chronic rheumatoid arthritis, osteoarthritis knees and destruction of joint tissues in similar diseases thereto, etc.), diabetic complications (retinopathy, nephropathy, neuropathy, macroangiopathy, etc.), chronic rheumatoid arthritis, osteoarthritis, rheumatoid myelitis, neurodegenerative diseases (Alzheimer's disease, Parkinson's disease, amyotrophic lateral sclerosis, AIDS encephalopathy, etc.), central nervous system disorders (disorders such as cerebral hemorrhage and cerebral infarction and the like, and sequelae or complications thereof, spinal cord injury, cerebral edema, encephalomyelitis, etc.), dementia dysmnesia, impaired consciousness, amnesia, anxiety symptoms, myotonia symptoms, ischemic peripheral circulatory disturbance, deep vein thrombosis, obstructive peripheral circulatory disturbance, arteriosclerosis obliterans, thromboangiitis obliterans, diabetic complications (neuropathy, nephropathy, retinopathy, cataract, macroangiopathy, osteopenia, diabetic hyperosmolar coma, infection, diabetic gangrene, oral dryness, decline in hearing, cerebrovascular accident, peripheral arterial disease, etc.), disturbance of metabolism or malnutrition (hyperlipidemia, hypercholesterolemia, low-HDL cholesterol, impaired glucose tolerance, etc.), insulin resistance syndrome, syndrome X, metabolic syndrome, cerebrovascular accident (asymptomatic cerebrovascular accident, transient ischemic attack, cerebral apoplexy, vascular dementia, hypertensive encephalopathy, cerebral infarction, etc.), cerebral edema, cerebral circulatory disturbance, recurrence and sequelae of cerebrovascular accident (neurological signs, mental signs, subjective symptoms, disturbance in activities of daily living, etc.), renal diseases (nephritis, glomerulonephritis, glomerulosclerosis, renal failure, thrombotic microangiopathy, diabetic nephropathy, nephrotic syndrome, hypertensive nephrosclerosis, complications of dialysis, organopathy including nephritis caused by radiation, etc.), eye diseases (glaucoma, ocular hypertension, etc.), thrombosis, multiple organ failure, endothelial dysfunction, hepatic diseases (hepatitis including hepatitis C, liver cirrhosis, etc.), gastrointestinal diseases (gastritis, gastric ulcer, stomach cancer, disorders after gastric surgery, esophageal ulcer, pancreatitis, colorectal polyp, cholelithiasis, inflammatory bowel disease (IBD), etc.), blood or hematopoietic diseases (polycythemia, vascular purpura, disseminated intravascular coagulation, multiple myeloma, etc.), urological or male genital diseases (cystitis, benign prostatic hyperplasia, sexually transmitted disease, etc.), gynecological diseases (climacteric disorder, gestosis, endometriosis, ovarian disease, mammary gland disease, sexually transmitted disease, etc.), infectious diseases (viral infection caused by cytomegalovirus, influenza virus, herpes virus or the like, rickettsial infection, bacterial infection, etc.), toxemia (sepsis, septic shock, endotoxin shock, gram negative sepsis, toxin shock syndrome, etc.), congenital diseases associated with sphingolipid accumulation (Fabry disease, Niemann-Pick disease (e.g., types A, B, C, D), Gaucher disease, Tay-Sachs disease)), skin diseases (contact dermatitis, etc.), painful affection (acute and chronic pain, persistent pain (alganesthesia, analgesia, etc.), etc.), inflammation-related diseases and immune-related diseases.

Particularly, the compound (I) can be useful as a prophylactic or therapeutic agent for cancer or a prophylactic or therapeutic agent for Niemann-Pick disease.

The compound (I) can be orally or parenterally administered as a medicament alone or with a pharmacologically acceptable carrier to a mammal (preferably a human).

Hereinafter, the medicament comprising the compound (I), which may be referred to as the "medicament of the present invention", will be described in detail. Examples of the dosage form of the medicament of the present invention include an oral preparation such as tablets (e.g., sugar-coated tablets, film-coated tablets, sublingual tablets, buccal tablets and rapidly orally disintegrating tablets), pills, granules, powders, capsules (e.g., soft capsules and microcapsules), syrups, emulsions, suspensions, films (e.g., orally disintegrating films and patch films for application to the oral mucosa) and the like. Other examples of the dosage form of the medicament of the present invention include a parenteral preparation such as injections, transfusions, transdermal preparations (e.g., iontophoresis dermal preparations), suppositories, ointments, transnasal preparations, transpulmonary preparations, eye drops and the like. Alternatively, the medicament of the present invention may be a controlled-release preparation such as a rapid-release preparation, a sustained-release preparation (e.g., a sustained-release microcapsule) or the like.

The medicament of the present invention can be produced by a known production method generally used in the field of pharmaceutical technology (e.g., a method described in Japanese Pharmacopoeia). If necessary, the medicament of the present invention can appropriately contain an appropriate amount of an additive usually used in the pharmaceutical field, such as an excipient, a binder, a disintegrant, a lubricant, a sweetener, a surfactant, a suspending agent, an emulsifier, a colorant, a preservative, a fragrance, a corrigent, a stabilizer, a viscosity modifier and the like.

Examples of the pharmacologically acceptable carrier described above include these additives.

For example, the tablets can be produced using an excipient, a binder, a disintegrant, a lubricant and the like. The pills and the granules can be produced using an excipient, a binder and a disintegrant. The powders and the capsules can be produced using an excipient and the like. The syrups can be produced using a sweetener and the like. The emulsions or the suspensions can be produced using a suspending agent, a surfactant, an emulsifier and the like.

Examples of the excipient include lactose, saccharose, glucose, starch, sucrose, microcrystalline cellulose, licorice powder, mannitol, sodium bicarbonate, calcium phosphate and calcium sulfate.

Examples of the binder include a solution containing 5 to 10% by weight of starch paste, a solution containing 10 to 20% by weight of gum arabic or gelatin, a solution containing 1 to 5% by weight of tragacanth, a carboxymethylcellulose solution, a sodium alginate solution and glycerin.

Examples of the disintegrant include starch and calcium carbonate.

Examples of the lubricant include magnesium stearate, stearic acid, calcium stearate and purified talc.

Examples of the sweetener include glucose, fructose, invert sugar, sorbitol, xylitol, glycerin and simple syrup.

Examples of the surfactant include sodium lauryl sulfate, polysorbate 80, sorbitan monofatty acid ester and polyoxyl 40 stearate.

Examples of the suspending agent include gum arabic, sodium alginate, carboxymethylcellulose sodium, methylcellulose and bentonite.

Examples of the emulsifier include gum arabic, tragacanth, gelatin and polysorbate 80.

When the medicament of the present invention is, for example, tablets, the tablets can be produced according to a method known per se in the art by adding, for example, an excipient (e.g., lactose, saccharose, starch), a disintegrant (e.g., starch, calcium carbonate), a binder (e.g., starch, gum arabic, carboxymethylcellulose, polyvinylpyrrolidone, hydroxypropylcellulose) or a lubricant (e.g., talc, magnesium stearate, polyethylene glycol 6000) to the compound (I) and molding the mixture by compression, followed by coating, if necessary, by a method known per se in the art for the purpose of taste masking, enteric properties or durability. For example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm GmbH, Germany, methacrylic acid-acrylic acid copolymer) and a dye (e.g., iron red, titanium dioxide) can be used as coating agents for the coating.

The injections include intravenous injections as well as subcutaneous injections, intracutaneous injections, intramuscular injections, intraperitoneal injections, drip injections and the like.

Such injections are prepared by a method known per se in the art, i.e., by dissolving, suspending or emulsifying the compound (I) in a sterile aqueous solution or oily solution. Examples of the aqueous solution include saline, an isotonic solution containing glucose or an additional adjuvant (e.g., D-sorbitol, D-mannitol, sodium chloride) and the like. The aqueous solution may contain an appropriate solubilizing agent, for example, an alcohol (e.g., ethanol), a polyalcohol (e.g., propylene glycol, polyethylene glycol) or a nonionic surfactant (e.g., polysorbate 80, HCO-50). Examples of the oily solution include sesame oil, soybean oil and the like. The oily solution may contain an appropriate solubilizing agent. Examples of the solubilizing agent include benzyl benzoate, benzyl alcohol and the like. The injections may be further supplemented with a buffer (e.g., a phosphate buffer solution, a sodium acetate buffer solution), a soothing agent (e.g., benzalkonium chloride, procaine hydrochloride), a stabilizer (e.g., human serum albumin, polyethylene glycol), a preservative (e.g., benzyl alcohol, phenol) or the like. Ampules are usually filled with the prepared injection solutions.

The content of the compound (I) in the medicament of the present invention may vary depending on the form of the preparation and is usually approximately 0.01 to approximately 100% by weight, preferably approximately 2 to approximately 85% by weight, more preferably approximately 5 to approximately 70% by weight, with respect to the whole preparation.

The content of the additive in the medicament of the present invention may vary depending on the form of the preparation and is usually approximately 1 to approximately 99.9% by weight, preferably approximately 10 to approximately 90% by weight, with respect to the whole preparation.

The compound (I) can be used stably, low toxically and safely. The daily dose of the compound (I) can vary depending on the status and body weight of a patient, the type of the compound, an administration route, etc. In the case of, for example, oral administration to a patient for the purpose of treating cancer, the daily dose in adult (body weight: approximately 60 kg) can be approximately 1 to approximately 1000 mg, preferably approximately 3 to approximately 300 mg, more preferably approximately 10 to approximately 200 mg, of the compound (I), which can be administered once or in two or three times.

In the case of parenterally administering the compound (I), the compound (I) is usually administered in the form of a solution (e.g., an injection). The single dose of the compound (I) also can vary depending on a recipient, a target organ, symptoms, an administration method, etc. For example, usually approximately 0.01 to approximately 100 mg, preferably approximately 0.01 to approximately 50 mg, more preferably approximately 0.01 to approximately 20 mg, of the compound (I) per kg of body weight can be administered by intravenous injection.

The compound (I) can be used in combination with an additional drug. Specifically, the compound (I) can be used in combination with a drug such as a hormone therapeutic, a chemotherapeutic, an immunotherapeutic, an agent of inhibiting activity of a cell growth factor and its receptor, or the like. The compound (I) can be further used in combination with an enzyme replacement therapeutic, a Chaperone therapeutic, a substrate reduction therapeutic, a cyclodextrin preparation, gene therapy to express a therapeutic enzyme protein, or cell therapy such as bone marrow transplantation and the like, for congenital diseases associated with sphingolipid accumulation (including Niemann-Pick disease) or the like. Hereinafter, the drug that may be used in combination with the compound (I) is referred to as a concomitant drug.

Examples of the "hormone therapeutic" that may be used include fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogen (e.g., tamoxifen citrate, toremifene citrate), contraceptive pills, mepitiostane, testololactone, aminoglutethimide, LH-RH agonists (e.g., goserelin acetate, buserelin, leuprorelin acetate), droloxifene, epitiostanol, ethinyl estradiol sulfonate, aromatase inhibitors (e.g., fadrozole hydrochloride, anastrozole, letrozole, exemestane, vorozole, formestane), anti-androgen (e.g., flutamide, bicalutamide, nilutamide, enzalutamide), 5α-reductase inhibitors (e.g., finasteride, epristeride, dutasteride), adrenal corticosteroid agents (e.g., dexamethasone, prednisolone, betamethasone, triamcinolone), androgen synthesis inhibitors (e.g., abiraterone), retinoid and agents delaying retinoid metabolism (e.g., liarozole), thyroid hormones and DDS (drug delivery system) preparations thereof.

Examples of the "chemotherapeutic" that may be used include an alkylating agent, an antimetabolite, an anticancer antibiotic and a plant-derived anticancer agent.

Examples of the "alkylating agent" that may be used include nitrogen mustard, nitrogen mustard-N-oxide hydrochloride, chlorambucil, cyclophosphamide, ifosfamide, thiotepa, carboquone, improsulfan tosilate, busulfan, nimustine hydrochloride, mitobronitol, melphalan, dacarbazine, ranimustine, estramustine sodium phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, Ribomustin, temozolomide, treosulfan, trofosfamide, zinostatin stimalamer, adozelesin, cystemustine, bizelesin and DDS preparations thereof.

Examples of the "antimetabolite" that may be used include mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, galocitabine, emitefur, capecitabine), aminopterin, nelarabine, leucovorin calcium, Tabloid, butocine, calcium folinate, calcium levofolinate, cladribine, emitefur, fludarabine, gemcitabine, hydroxycarbamide, pentostatin, piritrexim, idoxuridine, mitoguazone, tiazofurin, ambamustine, bendamustine and DDS preparations thereof.

Examples of the "anticancer antibiotic" that may be used include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride and DDS preparations (e.g., PEG liposomal doxorubicin) thereof.

Examples of the "plant-derived anticancer agent" that may be used include etoposide, etoposide phosphate, vinblastine sulfate, vincristine sulfate, vindesine sulfate, teniposide, paclitaxel, docetaxel, cabazitaxel, vinorelbine and DDS preparations thereof.

Examples of the "immunotherapeutic" that may be used include picibanil, Krestin, schizophyllan, lentinan, ubenimex, interferon, interleukin, macrophage colony-stimulating factor, granulocyte colony-stimulating factor, erythropoietin, lymphotoxin, BCG vaccines, *Corynebacterium parvum*, levamisole, polysaccharide K, procodazol, anti-CTLA4 antibodies (e.g., ipilimumab, tremelimumab), anti-PD-1 antibodies (e.g., nivolumab, pembrolizumab) and anti-PD-L1 antibodies.

The "cell growth factor" in the "agent of inhibiting activity of a cell growth factor and its receptor" can be any substance that promotes the growth of cells. Typical examples thereof include a factor that is a peptide having a molecular weight of 20,000 or smaller and exerts its activity at a low concentration through binding to its receptor. Specific examples of the cell growth factor that may be used include (1) EGF (epidermal growth factor) or a substance having activity substantially identical thereto [e.g., TGFα], (2) insulin or a substance having activity substantially identical thereto [e.g., insulin, IGF (insulin-like growth factor)-1, IGF-2], (3) FGF (fibroblast growth factor) or a substance having activity substantially identical thereto [e.g., acidic FGF, basic FGF, KGF (keratinocyte growth factor), FGF-10], and (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor 13), HGF (hepatocyte growth factor), VEGF (vascular endothelial growth factor), heregulin, angiopoietin].

The "receptor of the cell growth factor" can be any receptor having the ability to bind to any of the cell growth factor described above. Specific examples of the receptor that may be used include EGF receptor, heregulin receptor (e.g., HER3), insulin receptor, IGF receptor-1, IGF receptor-2, FGF receptor-1 or FGF receptor-2, VEGF receptor, angiopoietin receptor (e.g., Tie2), PDGF receptor and the like.

Examples of the "agent of inhibiting activity of a cell growth factor and its receptor" that may be used include EGF inhibitors, TGFα inhibitors, heregulin inhibitors, insulin inhibitors, IGF inhibitors, FGF inhibitors, KGF inhibitors, CSF inhibitors, EPO inhibitors, IL-2 inhibitors, NGF inhibitors, PDGF inhibitors, TGFβ inhibitors, HGF inhibitors, VEGF inhibitors, angiopoietin inhibitors, EGF receptor inhibitors, HER2 inhibitors, HER4 inhibitors, insulin receptor inhibitors, IGF-1 receptor inhibitors, IGF-2 receptor inhibitors, FGF receptor-1 inhibitors, FGF receptor-2 inhibitors, FGF receptor-3 inhibitors, FGF receptor-4 inhibitors, VEGF receptor inhibitors, Tie-2 inhibitors, PDGF receptor inhibitors, Abl inhibitors, Raf inhibitors, FLT3 inhibitors, c-Kit inhibitors, Src inhibitors, PKC inhibitors, Smo inhibitors, ALK inhibitors, ROR1 inhibitors, Trk inhibitors, Ret inhibitors, mTOR inhibitors, Aurora inhibitors, PLK inhibitors, MEK (MEK1/2) inhibitors, MET inhibitors, CDK inhibitors, Akt inhibitors, ERK inhibitors, PI3K inhibitors and the like. More specific examples of the agent that may be used include anti-VEGF antibodies (e.g., bevacizumab, ramucirumab), anti-HER2 antibodies (e.g., trastuzumab, pertuzumab), anti-EGFR antibodies (e.g., cetuximab, panitumumab, matuzumab, nimotuzumab), anti-HGF antibodies, imatinib, erlotinib, gefitinib, sorafenib, sunitinib, dasatinib, lapatinib, vatalanib, ibrutinib, bosutinib, cabozantinib, crizotinib, alectinib, vismodegib, axitinib, motesanib, nilotinib, 6-[4-(4-ethylpiperazin-1-ylmethyl)phenyl]-N-[1(R)-phenylethyl]-7H-pyrrolo[2,3-d]pyrimidin-4-amine (AEE-788), vandetanib, temsirolimus, everolimus, enzastaurin, tozasertib, phosphoric acid 2-[N-[3-[4-[5-[N-(3-fluorophenyl)carbamoylmethyl]-1H-pyrazol-3-ylamino]quinazolin-7-yloxy]propyl]-N-ethylamino]ethyl ester (AZD-1152), 4-[9-chloro-7-(2,6-difluorophenyl)-5H-pyrimido[5,4-d][2] benzazapin-2-ylamino]benzoic acid, N-[2-methoxy-5-[(E)-2-(2,4,6-trimethoxyphenyl)vinylsulfonylmethyl]phenyl] glycine sodium salt (ON-1910Na), volasertib, selumetinib, trametinib, N-[2(R),3-dihydroxypropoxy]-3,4-difluoro-2-(2-fluoro-4-iodophenylamino)benzamide (PD-0325901), bosutinib, regorafenib, afatinib, idelalisib, ceritinib, dabrafenib and the like.

Examples other than the drugs described above include L-asparaginase, L-arginase, arginine deiminase, aceglatone, procarbazine hydrochloride, protoporphyrin-cobalt complex salt, mercury hematoporphyrin-sodium, topoisomerase I inhibitors (e.g., irinotecan, topotecan, indotecan, indimitecan), topoisomerase II inhibitors (e.g., sobuzoxane), differentiation inducers (e.g., retinoid, vitamins D), other angiogenesis inhibitors (e.g., fumagillin, shark extracts, COX-2 inhibitors), α-blockers (e.g., tamsulosin hydrochloride), bisphosphonic acids (e.g., pamidronate, zoledronate), thalidomide, lenalidomide, pomalidomide, 5-azacytidine, decitabine, proteasome inhibitors (e.g., bortezomib, carfilzomib, ixazomib), NEDD8 inhibitors (e.g., pevonedistat), UAE inhibitors, PARP inhibitors (e.g., olaparib, niraparib, veliparib), antitumor antibodies such as anti-CD20 antibodies (e.g., rituximab, obinutuzumab), anti-CCR4 antibodies (e.g., mogamulizumab) and the like, antibody-drug conjugates (e.g., trastuzumab emtansine, brentuximab vedotin) or the like.

Examples of the "enzyme replacement therapeutic" include agalsidase α, agalsidase β, olipudase alfa, alglucerase and the like.

Examples of the "Chaperone therapeutic" include migalastat and the like.

Examples of the "substrate reduction therapeutic" include miglustat and the like.

Examples of the "cyclodextrin preparation" include hydroxyprolyl-β, γ-cyclodextrin and the like.

Examples of the "gene therapy" include a treatment method which involves transferring a vector of adeno-associated virus (AAV) or the like to a normal gene, and the like.

Examples of the "cell therapy" include a therapeutic method which involves transplanting hematopoietic stem cell source such as a bone marrow stem cell, a peripheral blood stem cell or the like.

A combination of the compound (I) and the concomitant drug can produce excellent effects such as: (1) the dose of the compound (I) or the concomitant drug can be reduced as compared with the administration of the compound (I) or the concomitant drug alone; (2) the concomitant drug can be selected for combined use with the compound (I) according to the symptoms (mild, serious, etc.) of a patient; (3) the period of treatment can be set longer; (4) a sustained therapeutic effect can be achieved; (5) a synergistic effect can be obtained by the combined use of the compound (I) and the concomitant drug; and the like.

Hereinafter, a combination of the compound (I) and the concomitant drug is referred to as a "combination drug of the present invention".

For use of a combination drug of the present invention, the time of administration of the compound (I) and the time of administration of the concomitant drug are not limited, and the compound (I) and the concomitant drug may be administered simultaneously or in a staggered manner to a recipient. In the case of administration in a staggered manner, the staggered manner may vary depending on active ingredients to be administered, a dosage form and an administration method. In the case of first administering, for example, the concomitant drug, the compound (I) can be administered within 1 minute to 3 days, preferably within 10 minutes to 1 day, more preferably within 15 minutes to 1 hour, after the administration of the concomitant drug. In the case of first administering the compound (I), the concomitant drug can be administered within 1 minute to 1 day, preferably within 10 minutes to 6 hours, more preferably within 15 minutes to 1 hour, after the administration of the compound (I). The dose of the concomitant drug can abide by a dose clinically used and can be appropriately selected according to a recipient, an administration route, a disease, a combination, etc.

Examples of the administration mode of the compound (I) and the concomitant drug used in combination include (1) the administration of a single preparation obtained by simultaneously formulating the compound (I) and the concomitant drug, (2) the simultaneous administration through the same administration route of two preparations obtained by separately formulating the compound (I) and the concomitant drug, (3) the administration through the same administration route in a staggered manner of two preparations obtained by separately formulating the compound (I) and the concomitant drug, (4) the simultaneous administration through different administration routes of two preparations obtained by separately formulating the compound (I) and the concomitant drug, and (5) the administration through different administration routes in a staggered manner of two preparations obtained by separately formulating the compound (I) and the concomitant drug (e.g., administration in the order of the compound (I) and then the concomitant drug, or in the reverse order).

The dose of the concomitant drug can be appropriately selected on the basis of a dose clinically used. The mixing ratio between the compound (I) and the concomitant drug can be appropriately selected depending on a recipient, an administration route, a target disease, symptoms, a combination, etc. When the recipient is, for example, a human, 0.01 to 100 parts by weight of the concomitant drug can be used with respect to 1 part by weight of the compound (I).

The compound (I) or the combination drug of the present invention can be further used in combination with a non-drug therapy. Specifically, the compound (I) or the combination drug of the present invention may be combined with a non-drug therapy, for example, (1) surgery, (2) induced hypertension chemotherapy using angiotensin II or the like, (3) gene therapy, (4) thermotherapy, (5) cryotherapy, (6) laser cauterization or (7) radiotherapy.

The compound (I) or the combination drug of the present invention is used, for example, before or after the surgery or the like or before or after treatment involving two or three of these therapies in combination to produce effects such as prevention of development of resistance, prolonged disease-free survival, inhibition of cancer metastasis or recurrence, life prolongation and the like.

Also, the treatment with the compound (I) or the combination drug of the present invention may be combined with supportive care [(i) the administration of an antibiotic (e.g., a 3-lactam antibiotic such as Pansporin and the like, a macrolide antibiotic such as clarithromycin and the like) against various intercurrent infections, (ii) the administration of a high-calorie infusion, an amino acid preparation or multivitamin for the improvement of malnutrition, (iii) the administration of morphine for pain relief, (iv) the administration of a drug improving adverse reactions such as nausea, vomiting, anorexia, diarrhea, leukopenia, thrombocytopenia, decreased hemoglobin concentration, alopecia, liver damage, kidney damage, DIC, fever and the like and (v) the administration of a drug for inhibiting multidrug resistance of cancer, etc.].

The present invention will be described further specifically with reference to Examples, Test Examples and Formulation Examples given below. However, the present invention is not intended to be limited by them, and various changes or modifications may be made therein without departing from the scope of the present invention.

EXAMPLES

In Examples below, the term "room temperature" usually means approximately 10° C. to approximately 35° C. A ratio used for a mixed solvent represents a volume ratio unless otherwise specified. % represents % by weight unless otherwise specified.

The term "NH" in silica gel column chromatography represents that an aminopropylsilane-bound silica gel was used. A ratio used for elution solvents represents a volume ratio unless otherwise specified.

In Examples below, the following abbreviations are used:
MS: mass spectrum
M: molar concentration
DMSO-$d_6$: deuterated dimethyl sulfoxide
$^1$H NMR: proton nuclear magnetic resonance
LC/MS: liquid chromatograph-mass spectrometer
ESI: electrospray ionization
APCI: atmospheric pressure chemical ionization
DMF: N,N-dimethylformamide
HATU: 2-(7-azabenzotriazol-1-yl)-1,1,3,3-tetramethyluronium hexafluorophosphate
THF: tetrahydrofuran $^1$H NMR was measured by Fourier transform NMR. ACD/SpecManager (trade name) or the like was used in analysis. No mention was made about the very broad peaks of protons of a hydroxy group, an amino group and the like.

MS was measured by LC/MS. ESI or APCI was used as an ionization method. Data was indicated by actually measured values (found). In general, molecular ion peaks ([M+H]$^+$, [M−H]$^-$ and the like) are observed. For example, in the case of a compound having a tert-butoxycarbonyl group, a fragment ion peak derived from the elimination of the tert-butoxycarbonyl group or the tert-butyl group is observed. In the case of a compound having a hydroxy group, a fragment ion peak derived from the elimination of H$_2$O may be observed. In the case of a salt, a molecular ion peak or fragment ion peak of a free form is usually observed.

Example 1

N-((3S,4R)-1-((8-Chloroquinoxalin-6-yl)carbonyl)-3-(4-fluorophenyl)piperidin-4-yl)-1-methyl-5-(trifluoromethyl)-1H-pyrazole-3-carboxamide A) Methyl 8-chloroquinoxaline-6-carboxylate A mixture of methyl 3,4-diamino-5-chlorobenzoate (2.80 g), a 40% aqueous oxalaldehyde solution (2.43 g), methanol (20 mL) and THF (10 mL) was stirred overnight at room temperature. The reaction mixture was diluted with a saturated aqueous solution of sodium bicarbonate, followed by extraction with THF/ethyl acetate. The extract was washed with saturated brine and dried over anhydrous magnesium sulfate, and the solvent was distilled off under reduced pressure. The residue was washed with ethyl acetate to obtain the title compound (1.28 g).
MS: [M+H]$^+$ 222.8.

B) 8-Chloroquinoxaline-6-carboxylic Acid

A mixture of methyl 8-chloroquinoxaline-6-carboxylate (1.27 g), an 8 M aqueous sodium hydroxide solution (7.13 mL), methanol (2 mL) and THF (10 mL) was stirred at 50° C. for 10 hours. The reaction mixture was concentrated under reduced pressure, and the residue was washed with water and diisopropyl ether to obtain the title compound (1.11 g).
MS: [M+H]$^+$ 209.0.

C) Ethyl 3-((3-ethoxy-3-oxopropyl)amino)-2-(4-fluorophenyl)propanoate

To a solution of ethyl 2-(4-fluorophenyl)acetate (29 g) in DMF (120 mL), N,N-dimethylformamide dimethyl acetal (32 mL) was added at room temperature, and the mixture was stirred at 140° C. for 16 hours in a nitrogen atmosphere. β-Alanine ethyl ester hydrochloride (33 g) was added to the reaction mixture at room temperature, and the mixture was stirred at 80° C. for 2 hours. The solvent was distilled off under reduced pressure, and water was added thereto at room temperature, followed by extraction with ethyl acetate. The extract was washed with water and saturated brine and then dried over anhydrous magnesium sulfate, and the solvent was distilled off under reduced pressure. To a solution of the obtained residue in DMF (300 mL) and acetic acid (300 mL), sodium tetrahydroborate (36 g) was added gradually under ice cooling, and the mixture was stirred at room temperature for 1 hour. The reaction mixture was diluted with ethyl acetate (150 mL), and a 2 M aqueous sodium hydroxide solution (300 mL) was added slowly under ice cooling. Water (300 mL) was added to the reaction mixture, followed by extraction with ethyl acetate (100 mL, three times). The extract was washed with a saturated aqueous solution of potassium carbonate, water (100 mL, twice) and saturated brine (100 mL) and then dried over anhydrous magnesium sulfate, and the solvent was distilled off under reduced pressure. The residue was dissolved in ethyl acetate (500 mL), and oxalic acid (30 mL) was added thereto at room temperature, and the mixture was heated to reflux for 30 minutes. The deposit was collected by filtration and washed with ethyl acetate. The obtained solid was suspended in ethyl acetate and basified with an aqueous potassium carbonate solution, followed by extraction with ethyl acetate. The extract was washed with water and saturated brine and then dried over anhydrous magnesium sulfate, and the solvent was distilled off under reduced pressure to obtain the title compound (26 g).
MS: [M+H]$^+$ 312.1.

D) tert-Butyl 3-(4-fluorophenyl)-4-oxopiperidine-1-carboxylate

To a solution of ethyl 3-((3-ethoxy-3-oxopropyl)amino)-2-(4-fluorophenyl)propanoate (26 g) in THF (250 mL), 60% sodium hydride (60%, 11 g) was added under ice cooling, and the mixture was heated to reflux for 30 minutes in a nitrogen atmosphere. Water (250 mL) was added to the reaction mixture, followed by extraction with ethyl acetate (250 mL, 100 mL, three times). The extract was washed with saturated brine and then dried over anhydrous magnesium sulfate, and the solvent was distilled off under reduced pressure. A mixture of the obtained residue, concentrated hydrochloric acid (110 mL) and acetic acid (110 mL) was heated to reflux for 16 hours. The solvent was distilled off under reduced pressure.

To a solution of the obtained residue and triethylamine (35 mL) in THF (200 mL), di-tert-butyl dicarbonate (19 mL) was added at room temperature, and the mixture was stirred for 30 minutes. Water was added to the reaction mixture, followed by extraction with ethyl acetate. The extract was washed with water and saturated brine and then dried over anhydrous magnesium sulfate, and the solvent was distilled off under reduced pressure. The residue was purified by silica gel column chromatography (ethyl acetate/hexane) to obtain the title compound (15 g).
MS: [M−Boc+2H]$^+$194.1

E) tert-Butyl (3S,4R)-3-(4-fluorophenyl)-4-(((1R)-1-phenylethyl)amino)piperidine-1-carboxylate To a solution of tert-butyl 3-(4-fluorophenyl)-4-oxopiperidine-1-carboxylate (11 g) and (1R)-1-phenylethanamine (6.1 mL) in toluene (120 mL), aluminum chloride (0.34 g) was added, and the mixture was heated to reflux for 16 hours in a nitrogen atmosphere. The solvent was distilled off under reduced pressure. A mixture of the obtained residue, a developed nickel catalyst (2.1 g) and ethanol (55 mL) was stirred at room temperature for 24 hours in a hydrogen atmosphere (0.5 MPa). The reaction mixture was filtered, and the solvent in the filtrate was distilled off under reduced pressure. The residue was suspended in toluene, and the solid was filtered off. The solvent in the filtrate was distilled off under reduced pressure, and the residue was purified by silica gel column chromatography (ethyl acetate/hexane) to obtain the title compound (2.4 g).

MS: $[M+H]^+$ 399.1

F) tert-Butyl (3S,4R)-4-amino-3-(4-fluorophenyl)piperidine-1-carboxylate

A mixture of tert-butyl (3S,4R)-3-(4-fluorophenyl)-4-(((1R)-1-phenylethyl)amino)piperidine-1-carboxylate (2.4 g), 10% palladium-carbon (1.1 g), methanol (30 mL) and acetic acid (3 mL) was stirred at room temperature for 6 hours in a hydrogen atmosphere (1 atm). The reaction mixture was filtered, and the solvent in the filtrate was distilled off under reduced pressure. The residue solid was collected by filtration and washed with hexane to obtain the title compound (0.95 g).

MS: $[M-tBu+2H]^+$ 238.9

G) tert-Butyl (3S,4R)-3-(4-fluorophenyl)-4-(1-methyl-5-(trifluoromethyl)-1H-pyrazole-3-carboxamide)piperidine-1-carboxylate A mixture of tert-butyl (3S,4R)-4-amino-3-(4-fluorophenyl)piperidine-1-carboxylate (275 mg), 1-methyl-5-(trifluoromethyl)-1H-pyrazole-4-carboxylic acid (236 mg), HATU (497 mg), triethylamine (0.3 mL) and DMF (4 mL) was stirred at room temperature for 15 hours. The reaction mixture was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (ethyl acetate/hexane) to obtain the title compound (403 mg).

MS: $[M-H]^-$ 469.3

H) N-((3S,4R)-3-(4-Fluorophenyl)piperidin-4-yl)-1-methyl-5-(trifluoromethyl)-1H-pyrazole-3-carboxamide Hydrochloride To a solution of tert-butyl (3S,4R)-3-(4-fluorophenyl)-4-(1-methyl-5-(trifluoromethyl)-1H-pyrazole-3-carboxamide)piperidine-1-carboxylate (395 mg) in methanol (2 mL), a 4 M solution of hydrogen chloride in ethyl acetate (2 mL) was added at room temperature, and the mixture was stirred at room temperature for 4 hours. The reaction mixture was concentrated under reduced pressure to obtain the title compound (336 mg).

MS: $[M+H]^+$ 371.2

I) N-((3S,4R)-1-((8-Chloroquinoxalin-6-yl)carbonyl)-3-(4-fluorophenyl)piperidin-4-yl)-1-methyl-5-(trifluoromethyl)-1H-pyrazole-3-carboxamide A mixture of N-((3 S,4R)-3-(4-fluorophenyl)piperidin-4-yl)-1-methyl-5-(trifluoromethyl)-1H-pyrazole-3-carboxamide hydrochloride (329 mg), 8-chloroquinoxaline-6-carboxylic acid (219 mg), HATU (431 mg), triethylamine (0.4 mL) and DMF (4 mL) was stirred at room temperature for 15 hours. The reaction mixture was diluted with a saturated aqueous solution of sodium bicarbonate, followed by extraction with ethyl acetate. The extract was washed with saturated brine and dried over anhydrous magnesium sulfate, and the solvent was distilled off under reduced pressure. The residue was purified by silica gel column chromatography (ethyl acetate/hexane) and then washed with ethyl acetate/hexane to obtain the title compound (305 mg).

MS: $[M+H]^+$ 561.1

$^1$H NMR (300 MHz, DMSO-$d_6$) δ 1.60-2.08 (2H, m), 3.36-3.45 (1H, m), 3.48-3.90 (2H, m), 3.93-4.34 (5H, m), 4.50-4.68 (1H, m), 6.97-7.09 (1H, m), 7.09-7.27 (3H, m), 7.28-7.41 (1H, m), 7.97 (1H, d, J=18.6 Hz), 8.07-8.23 (2H, m), 9.00-9.22 (2H, m).

Formulation Example 1

Each medicament containing the compound of the present invention as an active ingredient can be produced, for example, according to the following recipe:

TABLE 1

| 1. Capsule | |
| --- | --- |
| (1) Compound obtained in Example 1 | 40 mg |
| (2) Lactose | 70 mg |
| (3) Microcrystalline cellulose | 9 mg |
| (4) Magnesium stearate | 1 mg |
| One capsule | 120 mg |

The components (1), (2) and (3) and a ½ amount of the component (4) are mixed and then granulated. The remaining amount of the component (4) is added thereto, and the whole is encapsulated in a gelatin capsule shell.

TABLE 2

| 2. Tablet | |
| --- | --- |
| (1) Compound obtained in Example 1 | 40 mg |
| (2) Lactose | 58 mg |
| (3) Corn starch | 18 mg |
| (4) Microcrystalline cellulose | 3.5 mg |
| (5) Magnesium stearate | 0.5 mg |
| One tablet | 120 mg |

The components (1), (2) and (3), a ⅔ amount of the component (4) and a ½ amount of the component (5) are mixed and then granulated. The remaining amounts of the components (4) and (5) are added to this granule, which is then molded into a tablet by compression.

Formulation Example 2

50 mg of the compound obtained in Example 1 is dissolved in 50 mL of Japanese Pharmacopoeia distilled water for injection, and then, the amount of the solution is adjusted to 100 mL by the addition of Japanese Pharmacopoeia distilled water for injection. This solution is filtered under sterile conditions. Next, vials for injection are filled with this solution at 1 mL/vial under sterile conditions, freeze-dried, and hermetically sealed.

Test Example 1 SPT Enzyme Inhibition Test

Full-length human SPT1, human SPT2 and human ssSPTa used have amino acid sequences identical to NCBI Accession Nos. NM_006415, NM_004863 and NM_138288, respectively. pcDNA3.1 vectors having an inserted sequence of interest are prepared, and FreeStyle 293 cells (Life Technologies, Inc., Carlsbad, Calif., US) are cotransfected with the human SPT1, human SPT2, and human ssSPTa expression vectors according to the protocol of FreeStyle 293 Expression system. After culture for 3 days, the cells are recovered and frozen at −80° C. to obtain expressing cells. The frozen cells are suspended in a 50 mM Hepes buffer (pH 7.5) containing 250 mM sucrose, 5 mM ethylenediaminetetraacetic acid (EDTA), 5 mM dithiothreitol (DTT) and cOmplete, EDTA-free (Roche Applied Science, Penzberg, Upper Bavaria, Germany). The cells are disrupted (on ice, 20,000 rpm, 20 sec×2) using POLYTORON (Central Scientific Commerce, Inc.). After centrifugation at 2000 rpm (850×g) for 10 minutes, the supernatant is recovered. Subsequently, the supernatant is centrifuged at 40,000 rpm (186,010×g) for 60 minutes, and the supernatant is discarded. The pellets are suspended in a 50 mM Hepes buffer (pH 7.5) containing 5 mM EDTA, 5 mM DTT and cOmplete, EDTA-free, passed through a 40-µm cell strainer and stored at −80° C. The resultant is used as a SPT2-expressing membrane fraction. The protein concentration is determined using CBB Protein Assay with bovine serum albumin used as standards.

5 µL of each test compound is mixed with 10 µL of the 100 µg/mL SPT2-expressing membrane fraction using an assay buffer (100 mM Hepes (pH 8.0) containing 2.5 mM EDTA, 5 mM DTT and 0.01% fatty acid-free bovine serum albumin), and the mixture is left standing at room temperature for 60 minutes. Subsequently, 5 µL of a substrate solution containing 2 mM L-serine and 20 µM palmitoyl CoA is added thereto, and an enzyme reaction is carried out in a 384-well plate using 20 µL in total of the reaction system. After reaction at room temperature for 15 minutes, the reaction is terminated by the addition of 20 µL of a 2% aqueous formic acid solution. Subsequently, 40 µL of acetonitrile containing 600 nM C17-sphinganine (Avanti Polar Lipids, Inc., Alabaster, Ala., US) is added thereto as an internal standard. The reaction sample is subjected to on-line solid-layer extraction using RapidFire 300 (Agilent Technologies Inc., Santa Clara, Calif., US). The SRM transition of 3-ketodihydrosphingosine (reaction product) and C17-sphinganine (internal standard) is set to 300.5/270.3 and 288.4/60.2, respectively, on a positive SRM mode using API-4000 (AB SCIEX, Framingham, Mass., US) equipped with ESI probes. Mass chromatograms are obtained using Analyst software (version 1.5.0, AB SCIEX). Their mass chromatogram areas are respectively calculated, and the rate of inhibition (%) by the test compound is calculated using an area ratio (the value of the reaction product is divided by the value of the internal standard).

Test Example 2 HCC4006 Cell Growth Inhibition Test

A lung adenocarcinoma cell line HCC4006 (ATCC) is cultured using an RPMI-1640 medium (Wako Pure Chemical Industries, Ltd.) containing 10% fetal bovine serum and penicillin/streptomycin. 250 cells per well are inoculated into 40 µL of a medium in a 384-well culture plate. On the next day, 10 µL of a 1 µM solution of the compound of Example 1 is added to each well containing the cells. After culture for 5 days, the medium is discarded, and 30 µL of CellTiter-Glo Luminescent Cell Viability Assay solution (Promega Corp., Fitchburg, Wis., US) is added to each well. Light emission signals are measured using EnVision (PerkinElmer, Inc., Waltham, Mass., US). The rate of inhibition (%) by the compound of Example 1 is calculated according to the following expression:

Rate of inhibition (%)=(1−(Count of the test compound−Blank)/(Control−Blank))×100

In the above expression, a count under compound non-addition conditions is indicated as a control, and a count under cell-free conditions is indicated as a blank.

Test Example 3 Efficacy Evaluation Test Using Niemann-Pick Disease Model Cell

A normal line and an acidic sphingomyelinase-deficient cell line (Niemann-Pick disease model cells), which is responsible for Niemann-Pick disease, are each cultured using Iscove's Modified Dulbecco's Medium containing 10% fetal bovine serum and penicillin/streptomycin. At the day following the inoculation to the culture plate, the medium is replaced, and the cells are cultured in a medium containing each SPT inhibitor for 4 days. After the culture, the medium is discarded, and sphingolipids such as sphingomyelin in the cells are extracted with hexane and quantified by use of TLC, gas chromatography or the like.

Test Example 4 Efficacy Evaluation Test Using Sphingomyelin Accumulation Model Mouse as Niemann-Pick Disease Type A and Type B Model A phase 1b clinical trial on Niemann-Pick disease type B which develops by abnormality in acid sphingomyelinase has reported that the administration of recombinant acid sphingomyelinase (olipudase alfa) decreased sphingomyelin accumulated in a peripheral organ such as the liver, and this led to the amelioration of the pathological condition (Am J Surg Pathol. 2016; 40: 1232).

Also, the intraperitoneal administration of an acid sphingomyelinase inhibitor, imipramine hydrochloride, to a mouse increases its enzyme substrate, sphingomyelin, not only in a peripheral organ such as the liver but in the central nervous system such as the cerebrum, and the mouse obtained by such administration is recognized as an animal model that can induce sphingomyelin accumulation, as in human Niemann-Pick disease type A and type B, in each tissue (Gen Physiol Biophys 2016; 35: 195).

Accordingly, the compound of the present invention was evaluated as a SPT inhibitor for its sphingomyelin-lowering effect on Niemann-Pick disease type B, and Niemann-Pick disease type A, which also accumulates sphingomyelin in the central nervous system such as the cerebral cortex, by the following method. Imipramine hydrochloride (Wako Pure Chemical Industries, Ltd.) was dissolved at a concentration of 2 mg/mL in saline and intraperitoneally administered at a dose of 40 mg/kg to each 6-week-old male C57BL/6J Jcl mouse (CLEA Japan, Inc.) for 2 weeks once daily. Then, the SPT inhibitor consisting of the compound of the present invention was orally administered as a 0.5% suspension in methylcellulose (MC) to each mouse (8 mice per group) for 2 weeks using the amount shown in the below table (which shows a single dose). In this operation, the intraperitoneal administration of imipramine hydrochloride was also carried out once daily concurrently therewith. After the completion of the administration of the SPT inhibitor, the cerebrum was excised from the mouse cranium and separated into the cortex and the medulla. The cortical portion was rapidly frozen in liquid nitrogen and then disrupted using Shake-Master Auto (Bio-Medical Science Co., Ltd.) under freezing. 2-Propanol (containing 0.002% of BHT (dibutylhydroxytoluene as a fat and oil antioxidant) was added thereto in an amount of 9 mL/g of wet weight, and lipids in the cerebral cortex were extracted by suspension using Shake-Master Auto again. The concentration of sphingomyelin contained in the 2-propanol was measured using a sphingomyelin assay kit (Abcam, Inc., ab138877) based on the fluorescence quantification method. EnVision 2102 Multilabel Reader (PerkinElmer Inc.) was used in fluorescence measurement.

The results of measuring the amount of sphingomyelin per wet weight of the cerebral cortex are shown in Table 3 below and FIG. 1.

TABLE 3

| Group No. | Imipramine hydrochloride (4 wk, once daily) | SPT inhibitor (2 wk, twice daily) | Amount of sphingomyelin per wet weight of cerebral cortex (µg/g) |
|---|---|---|---|
| 1 | Saline (20 mL/kg) | 0.5% MC | 3.300 ± 0.578 |
| 2 | 40 mg/20 mL/kg | 0.5% MC | 4.568 ± 0.742 |
| 3 | 40 mg/20 mL/kg | 0.3 mg/kg | 3.282 ± 0.260 |
| 4 | 40 mg/20 mL/kg | 1.0 mg/kg | 2.972 ± 0.635 |
| 5 | 40 mg/20 mL/kg | 3.0 mg/kg | 2.952 ± 0.219 |

(Mean ± S.D., N = 7-8)

Approximately 1.4-fold significant increase in sphingomyelin accumulation in the cerebral cortex was observed in a group that received the intraperitoneal administration of 40 mg/kg imipramine hydrochloride for 4 weeks once daily and the oral administration of 0.5% MC as a vehicle for 2 weeks twice daily (group 2) as compared with a control group that received the intraperitoneal administration of saline for 4 weeks (group 1) ($p<0.01$, Student's t-test). From this, it was able to be confirmed that a model mimicking Niemann-Pick disease type A and type B which accumulate sphingomyelin in the cerebral cortex was established by the intraperitoneal administration of imipramine hydrochloride for 4 weeks. Furthermore, the dose-dependent significant effect of suppressing sphingomyelin accumulation in the cerebral cortex was observed by oral administration of the SPT inhibitor consisting of the compound of the present invention for 2 weeks twice daily at a single dose of 0.3 (group 3), 1.0 (group 4) and 3.0 mg/kg (group 5) ($p<0.025$, one-tailed Williams' test). These results suggested the possibility that the SPT inhibitor consisting of the compound of the present invention has the effect of lowering sphingomyelin in the cerebral cortex and can serve as a therapeutic drug for human Niemann-Pick disease type A and type B.

INDUSTRIAL APPLICABILITY

The compound of the present invention can be used as a SPT inhibitor and can be useful as a prophylactic or therapeutic agent for SPT-related diseases including cancer and Niemann-Pick disease, and the like.

The invention claimed is:
1. N-((3S,4R)-1-((8-Chloroquinoxalin-6-yl)carbonyl)-3-(4-fluorophenyl)piperidin-4-yl)-1-methyl-5-(trifluoromethyl)-1H-pyrazole-3-carboxamide or a salt thereof.
2. A medicament comprising a compound or a salt thereof according to claim 1.
3. A method for inhibiting SPT in a mammal, comprising administering an effective amount of a compound or a salt thereof according to claim 1 to the mammal.
4. A method for treating Niemann-Pick disease in a mammal, comprising administering an effective amount of a compound or a salt thereof according to claim 1 to the mammal.
5. A method for treating Niemann-Pick disease type A or Niemann-Pick disease type B in a mammal, comprising administering an effective amount of a compound or a salt thereof according to claim 1 to the mammal.

* * * * *